(12) United States Patent
Tippana

(10) Patent No.: US 10,838,587 B2
(45) Date of Patent: Nov. 17, 2020

(54) AUGMENTED AND VIRTUAL REALITY FOR TRAVERSING GROUP MESSAGING CONSTRUCTS

(71) Applicant: Microsoft Technology Licensing, LLC, Redmond, WA (US)

(72) Inventor: Sreevani Tippana, Redmond, WA (US)

(73) Assignee: Microsoft Technology Licensing, LLC, Redmond, WA (US)

( * ) Notice: Subject to any disclaimer, the term of this patent is extended or adjusted under 35 U.S.C. 154(b) by 3 days.

(21) Appl. No.: 15/860,343

(22) Filed: Jan. 2, 2018

(65) Prior Publication Data

US 2019/0204994 A1 Jul. 4, 2019

(51) Int. Cl.
*G06F 3/0482* (2013.01)
*H04L 12/58* (2006.01)
*G06F 3/048* (2013.01)
*G06F 3/0484* (2013.01)
*G06Q 10/10* (2012.01)
(Continued)

(52) U.S. Cl.
CPC ............ *G06F 3/0482* (2013.01); *G06F 3/048* (2013.01); *G06F 3/04842* (2013.01); *G06F 3/167* (2013.01); *G06Q 10/10* (2013.01); *H04L 51/16* (2013.01); *H04L 51/22* (2013.01); *H04L 67/38* (2013.01); *A61B 5/744* (2013.01); *G06F 3/165* (2013.01); *G06T 11/60* (2013.01); *G06T 2200/24* (2013.01); *H04L 51/046* (2013.01)

(58) Field of Classification Search
CPC ............... G06F 3/0482; G06F 3/04842; G06F 3/04883; G06F 3/048; G06F 3/167; G06F 3/165; H04L 51/22; H04L 67/38; H04L 51/16; H04L 51/046; G06Q 10/10; A61B 5/744; G06T 2200/24; G06T 11/60
See application file for complete search history.

(56) References Cited

U.S. PATENT DOCUMENTS 5,884,029 A    3/1999  Brush, II et al.
7,386,799 B1 * 6/2008  Clanton ................ A63F 13/12
                                              715/758
(Continued)

OTHER PUBLICATIONS

Popper, Ben, "This is how Facebook will animate you in VR", Retrieved from<<https://www.theverge.com/2016/10/6/13176906/oculus-connect-3-facebook-social-vr-avatars>>, Oct. 6, 2016, 4 Pages.
(Continued)

*Primary Examiner* — Kieu D Vu
*Assistant Examiner* — Rami R Okasha

(57) ABSTRACT

In non-limiting examples of the present disclosure, systems, methods and devices for interacting with one or more electronic messages in a virtual space are presented. One or more avatars corresponding to the senders of a plurality electronic messages may be displayed within a virtual space. A user may navigate within the virtual space and execute one or more actions associated with an electronic message and/or its sender from the virtual space. In some examples, each of a plurality of electronic messages may be spatially arranged in the virtual space according to a corresponding message thread. In additional examples, each of a plurality of electronic messages may be spatially arranged in the virtual space based on a time that each message was sent or received.

18 Claims, 9 Drawing Sheets

(51) Int. Cl.
  *H04L 29/06* (2006.01)
  *A61B 5/00* (2006.01)
  *G06F 3/16* (2006.01)
  *G06T 11/60* (2006.01)

(56) References Cited

U.S. PATENT DOCUMENTS

| | | | | |
|---|---|---|---|---|
| 7,840,903 B1 * | 11/2010 | Amidon | ............ | G06F 3/04815 |
| | | | | 715/757 |
| 8,026,918 B1 * | 9/2011 | Murphy | ............ | G06N 3/006 |
| | | | | 345/473 |
| 8,502,825 B2 | 8/2013 | Zalewski et al. | | |
| 8,547,381 B2 * | 10/2013 | Murphy | ............ | G06N 3/006 |
| | | | | 345/473 |
| 8,589,792 B2 * | 11/2013 | Shuster | ............ | G06T 19/20 |
| | | | | 715/706 |
| 8,601,386 B2 * | 12/2013 | Altberg | ............ | H04L 12/66 |
| | | | | 715/706 |
| 8,930,825 B2 * | 1/2015 | Brugler | ............ | G06Q 10/107 |
| | | | | 715/752 |
| 9,098,167 B1 * | 8/2015 | Issa | ............ | G06F 3/04815 |
| 9,384,469 B2 * | 7/2016 | Alkov | ............ | A63F 13/57 |
| 9,402,057 B2 | 7/2016 | Kaytaz et al. | | |
| 9,454,747 B2 * | 9/2016 | Schultz | ............ | G06Q 10/10 |
| 9,569,075 B2 * | 2/2017 | Kyogoku | ............ | G06F 3/04842 |
| 10,082,928 B2 * | 9/2018 | Takeda | ............ | G06F 3/04817 |
| 2004/0179037 A1 | 9/2004 | Blattner et al. | | |
| 2006/0075055 A1 | 4/2006 | Littlefield | | |
| 2007/0101276 A1 * | 5/2007 | Yuen | ............ | G06F 16/954 |
| | | | | 715/757 |
| 2008/0215994 A1 * | 9/2008 | Harrison | ............ | A63F 13/10 |
| | | | | 715/757 |
| 2008/0281813 A1 * | 11/2008 | Moody | ............ | G06Q 10/107 |
| 2009/0055484 A1 * | 2/2009 | Vuong | ............ | G06Q 10/107 |
| | | | | 709/206 |
| 2010/0023878 A1 * | 1/2010 | Douris | ............ | H04L 12/6418 |
| | | | | 715/757 |
| 2010/0045660 A1 | 2/2010 | Dellinger et al. | | |
| 2010/0077034 A1 * | 3/2010 | Alkov | ............ | A63F 13/50 |
| | | | | 709/206 |
| 2010/0115426 A1 * | 5/2010 | Liu | ............ | G06Q 10/107 |
| | | | | 715/757 |
| 2011/0041082 A1 * | 2/2011 | Nguyen | ............ | G06Q 10/10 |
| | | | | 715/752 |
| 2011/0099476 A1 | 4/2011 | Snook et al. | | |
| 2011/0173553 A1 * | 7/2011 | Karmon | ............ | G06Q 10/107 |
| | | | | 715/767 |
| 2012/0011453 A1 * | 1/2012 | Shimono | ............ | G06Q 10/107 |
| | | | | 715/753 |
| 2012/0102037 A1 * | 4/2012 | Ozonat | ............ | G06F 16/334 |
| | | | | 707/738 |
| 2013/0227437 A1 * | 8/2013 | Brody | ............ | H04L 12/1822 |
| | | | | 715/757 |
| 2013/0293584 A1 * | 11/2013 | Anderson | ............ | G06T 11/00 |
| | | | | 345/633 |
| 2014/0168348 A1 * | 6/2014 | Kubota | ............ | G06Q 30/06 |
| | | | | 348/14.02 |
| 2014/0330550 A1 * | 11/2014 | Bill | ............ | G06Q 10/10 |
| | | | | 704/2 |
| 2015/0039704 A1 * | 2/2015 | Kursun | ............ | H04L 51/22 |
| | | | | 709/206 |
| 2015/0058708 A1 * | 2/2015 | Georgiev | ............ | G06F 17/248 |
| | | | | 715/202 |
| 2015/0254902 A1 * | 9/2015 | Macia | ............ | G06F 3/147 |
| | | | | 345/633 |
| 2016/0216941 A1 * | 7/2016 | Ramseur | ............ | G06F 3/167 |
| 2016/0234149 A1 * | 8/2016 | Tsuda | ............ | H04L 67/306 |
| 2017/0329779 A1 * | 11/2017 | Lewin-Eytan | ............ | H04L 51/22 |
| 2018/0083848 A1 * | 3/2018 | Siddiqi | ............ | H04L 43/045 |
| 2018/0095616 A1 * | 4/2018 | Valdivia | ............ | G06Q 50/01 |
| 2018/0246579 A1 * | 8/2018 | Kashihara | ............ | G06F 3/013 |

OTHER PUBLICATIONS

"International Search Report & Written Opinion Issued in PCT Application No. PCT/US2018/065572", dated Mar. 8, 2019, 14 Pages.

* cited by examiner

AUGMENTED AND VIRTUAL REALITY FOR TRAVERSING GROUP MESSAGING CONSTRUCTS

BACKGROUND

Advancements in computing technologies have brought down the costs associated with virtual reality, augmented reality, and mixed reality devices, providing a larger number of users with access to those devices and the computing environments that those devices may provide. Virtual reality, augmented reality, and mixed reality devices and their associated applications and platforms are capable of providing immersive user experiences which can make interacting with various computing environments more intuitive and interesting than was previously possible.

It is with respect to this general technical environment that aspects of the present technology disclosed herein have been contemplated. Furthermore, although a general environment has been discussed, it should be understood that the examples described herein should not be limited to the general environment identified in the background.

SUMMARY

This summary is provided to introduce a selection of concepts in a simplified form that are further described below in the Detailed Description section. This summary is not intended to identify key features or essential features of the claimed subject matter, nor is it intended to be used as an aid in determining the scope of the claimed subject matter. Additional aspects, features, and/or advantages of examples will be set forth in part in the description which follows and, in part, will be apparent from the description or may be learned by practice of the disclosure.

Non-limiting examples of the present disclosure describe systems, methods and devices for displaying and/or interacting with one or more electronic messages in a virtual space. In some examples, a method for interacting with one or more electronic messages is provided, the method comprising: displaying, on a display of a computing device, an electronic message thread, the electronic message thread comprising a plurality of electronic messages displayed in association with a plurality of avatars, wherein each of the plurality of avatars represents a sender of one of the plurality of electronic messages; displaying, in association with one of the avatars, a selectable option to have a corresponding one of the plurality of messages presented in a virtual space by the computing device; receiving an indication to present the corresponding electronic message in the virtual space; and presenting, by the computing device, the corresponding electronic message in the virtual space.

In another example, a system for interacting with one or more electronic messages is provided, the system comprising: a memory for storing executable program code; and one or more processors, functionally coupled to the memory, the one or more processors being responsive to computer-executable instructions contained in the program code and operative to: display, on the display of a virtual reality computing device, an electronic message thread, the electronic message thread comprising a plurality of electronic messages displayed in association with a plurality of avatars, wherein each of the plurality of avatars represents a sender of one of the plurality of electronic messages; display, on the display of the virtual reality computing device in association with one of the avatars, a selectable option to have a corresponding one of the plurality of electronic messages presented in a virtual space; receive, by the virtual reality computing device, an indication to present the corresponding electronic message in the virtual space; and present, on the virtual reality computing device, the corresponding electronic message in the virtual space.

In other examples, a computer-readable storage device is provided, the computer-readable storage device comprising executable instructions, that, when executed by one or more processors, assist with interacting with one or more electronic messages in a virtual space of a client computing device, the computer-readable storage device including instructions executable by the one or more processors for: receiving credentials associated with an electronic messaging account; identifying a plurality of electronic messages sent to a user associated with the electronic messaging account; causing, in the virtual space, a plurality of avatars to be displayed, wherein each of the plurality of avatars represents a sender of at least one of the plurality of electronic messages; receiving, from the client computing device, an indication to have one of the plurality of electronic messages presented in association with a corresponding one of the plurality of avatars; and causing the indicated electronic message to be presented, by the client computing device, in association with the corresponding avatar.

BRIEF DESCRIPTION OF THE DRAWINGS

Non-limiting and non-exhaustive examples are described with reference to the following figures.

DETAILED DESCRIPTION

Figure 1:
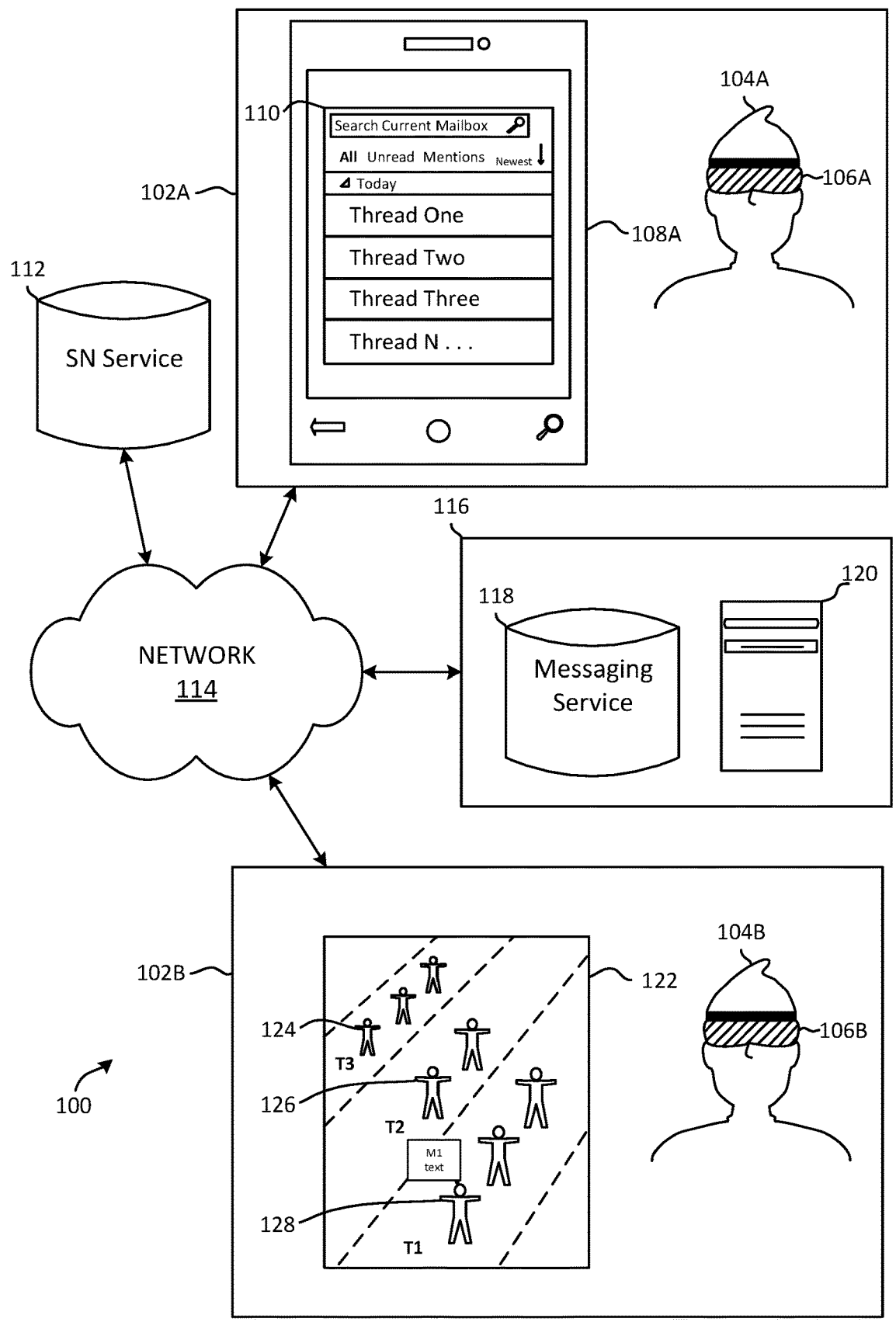
FIG. 1 is a schematic diagram illustrating an example distributed computing environment for interacting with one or more electronic messages in a virtual space presented by a client computing device.

Various embodiments will be described in detail with reference to the drawings, wherein like reference numerals represent like parts and assemblies throughout the several views. Reference to various embodiments does not limit the scope of the claims attached hereto. Additionally, any examples set forth in this specification are not intended to be limiting and merely set forth some of the many possible embodiments for the appended claims.

The various embodiments and examples described above are provided by way of illustration only and should not be construed to limit the claims attached hereto. Those skilled in the art will readily recognize various modifications and changes that may be made without following the example embodiments and applications illustrated and described herein, and without departing from the true spirit and scope of the claims.

Generally, the present disclosure is directed to systems, methods and devices for displaying and interacting with one or more electronic messages in a virtual space provided by a client computing device. In some examples, the virtual space may comprise a virtual environment displayed by a virtual reality computing device. In other examples, the virtual space may comprise an augmented environment displayed by an augmented reality device. In still other examples, the virtual space may comprise a virtual environment and/or an augmented environment displayed by a mixed reality computing device. As used herein, a client computing device utilized by an accessing user to view and interact with one or more electronic messages, attachments of one or more electronic messages, sender avatars, and/or sending users of one or more electronic messages, may comprise a virtual reality computing device, an augmented reality computing device, or a mixed reality computing device. The systems, methods, and devices described herein may be utilized to view and/or otherwise interact with electronic messages comprising one or more of: SMS messages, email messages, application feed messages and posts (e.g., Twitter messages and feeds, Facebook messages and feeds, etc.), etc.

According to examples, an accessing user may utilize a client computing device to input credentials for accessing one or more messaging service accounts that the accessing user is associated with. Upon receiving the credentials, a virtual messaging service may identify one or more electronic messages that were sent to the accessing user's messaging service account for which the user's credentials grant access to. The virtual messaging service may cause one or more of the identified electronic messages, attachments associated with identified electronic messages, one or more sender avatars corresponding to one or more identified electronic messages, and information associated with sending users corresponding to the one or more sending avatars, to be displayed within a virtual space of a virtual messaging application user interface executed on the accessing user's client computing device.

In some examples, upon identifying one or more electronic messages sent to an accessing user's messaging service account, the virtual messaging service may cause at least a portion of one or more of those messages to be displayed within a virtual space presented by a client computing device. In some examples, an avatar corresponding to a sender of each of the one or more messages may be displayed in the virtual space. For example, if a first thread corresponding to a first set of messages is identified based on an accessing user's credentials, a plurality of avatars corresponding to the sending users of the first set of messages may be spatially arranged in the virtual space, and the accessing user may virtually navigate and interact with each avatar and/or corresponding message of the first thread within the virtual space. Likewise, if a second thread corresponding to a second set of messages is identified based on the accessing user's credentials, a plurality of avatars corresponding to the sending users of the second set of messages may be spatially arranged in the virtual space, and the accessing user may virtually navigate and interact with each avatar and/or corresponding message of the first and second threads within the virtual space.

In examples, each electronic message and/or corresponding avatar associated with an electronic message thread may be spatially arranged such that an electronic message sent to an accessing user at a more recent time is closer to a virtual instance (e.g., a virtual point of view) of the accessing user within the virtual space than each electronic message of the electronic message thread that is sent to the accessing user at a less recent time. Similarly, each electronic message thread for which an electronic message has been sent to an accessing user at a more recent time may be spatially arranged such that the corresponding thread is closer to a virtual instance of the accessing user within the virtual space than each other message thread for which an electronic message has been sent to the accessing user less recent time.

According to some aspects, an accessing user may interact with each electronic message and/or corresponding avatar displayed within a virtual space. In some examples, an accessing user may be presented with a selectable option to view all or a portion of an electronic message associated with a virtual space. In additional examples, an accessing user may be presented with a selectable option to have all or a portion of the text associated with an electronic message audibly read by a sending avatar of the electronic message in a virtual space. In additional examples an accessing user may be presented with selectable options to reply or delete an electronic message presented in a virtual space. In still other examples an accessing user may be presented with selectable options to start a text messaging dialog, an audio messaging dialog and/or a video messaging dialog with a sender of an electronic message from within a virtual space.

FIG. 1 is a schematic diagram illustrating an example distributed computing environment 100 for interacting with one or more electronic messages in a virtual space presented by a virtual messaging application executed by a client computing device. Distributed computing environment 100 includes first client device environment 102A, social network service database 112, network 114, electronic messaging service and processing environment 116, and second client device environment 102B.

First client device environment 102A includes accessing user 104A, wearing virtual reality computing device 106A, and client computing device 110. A typical user interface for an electronic messaging application, such as an email application, is displayed on client computing device 110. The electronic messaging application user interface on client computing device 110 is shown for illustrative purposes to depict the difference between interacting with electronic messages in that typical application format compared with the virtual or augmented format of the current application in relation to the virtual messaging application and/or virtual messaging service described herein. For example, the electronic messaging application user interface on client computing device 110 shows a plurality of electronic message threads in a list format, which may be ordered in various manners, such as by most recent, most relevant to a search, etc. The electronic messaging application user interface on client computing device 100 also includes a search bar element that a user may enter one or more queries in to locate electronic messages relevant to that query. A user may click on one or more of the threads to view one or more emails in that thread, and additional information about those emails, such as the senders of those emails, the content of those emails, whether those emails contain attachments, etc.

According to aspects of the current disclosure, user 104A may provide credentials to access one or more messaging services, via network 114, to a virtual messaging service comprised in electronic messaging service and processing environment 116. For example, user 104A may be the owner or administrator of one or more messaging service accounts, such as email services, SMS messages, etc., and user 104A may provide one or more credentials (e.g., passwords) associated with those one or more message service accounts from a computing device, such as virtual reality computing device 106A and/or client computing device 102A, via network 114, to a virtual messaging service comprised in electronic messaging service and processing environment 116. One or more computing devices in electronic messaging service and processing environment 116, such as server computing device 120, may receive user 104A's credentials and request that one or more messages from associated electronic messaging services associated with user 104A's credentials be sent to a virtual messaging service comprised in electronic messaging service and processing environment 116.

In some examples, the electronic messaging services that user 104A has access to via user 104A's credentials may be comprised within electronic messaging service and processing environment 116, thus eliminating the need for requesting the one or more messages from non-affiliated electronic messaging services. In additional examples, the virtual messaging service may store an accessing user's credentials, and need not receive a new set of credentials from a same accessing user each time new electronic messages are to be requested from one or more associated electronic messaging services. In some examples, server computing device 120 in electronic messaging service and processing environment 116 may not need to make explicit calls to messaging services to request electronic messages associated with the credentials of user 104A. Rather, a pull mechanism may be utilized by the virtual messaging service comprised in electronic messaging service and processing environment 116 such that messages from one or more electronic messaging services are periodically pulled from those one or more electronic messaging services. In additional examples, a push mechanism may be utilized such that when a new message arrives at one or more electronic messaging services, that new message is automatically sent from the one or more electronic messaging services to the virtual messaging service comprised within electronic messaging service and processing environment 116.

User 104B in second client device environment 102B is the same user as user 104A, and wears the same virtual reality computing device 106B as depicted as virtual reality computing device 106A in first client device environment 102A. However, in second client device environment 102A, user 104B has made a request to the virtual messaging service in messaging service and processing environment 116, via virtual reality computing device 106B, and network 114, to view one or more electronic messages associated with user 104A's credentials in a virtual space provided by a virtual messaging application executed by virtual reality computing device 106B. In examples, user 104B may make a request to view one or more electronic messages associated with user 104A's credentials in a virtual space provided by the virtual messaging application executed by virtual reality computing device 106B simply by inputting user 104A's credentials to access one or more messaging services into virtual reality computing device 106B (e.g., audible input of those credentials into virtual reality computing device 106B, gesture input of those credentials into virtual reality computing device 106B, Bluetooth or physically connected input device input into virtual reality computing device 106B, etc.).

Upon receiving such a request, one or more computing devices in electronic messaging service and processing environment 116 associated with a virtual messaging service, such as server computing device 120, may identify one or more electronic messages from one or more related messaging services as described above, and cause a virtual space 122 including at least one of those messages to be displayed on virtual reality computing device 106B. Virtual space 122 includes a plurality of message threads (e.g., T1, T2, T3), and each of the plurality of message threads comprises at least one electronic message sent to an electronic messaging service account that user 104B's input credentials are associated with. In this specific example, a first message thread, T1, is shown in virtual space 122 with three avatars corresponding to the senders of messages in message thread T1, which are depicted closer to a virtual instance (e.g., a virtual point of view) of user 104B in the virtual space 122 than the two avatars corresponding to the senders of messages in message thread T2, which are depicted closer to the virtual instance of user 104B in the virtual space 122 than the three avatars corresponding to the senders of messages in message thread T1.

In some examples, the message threads depicted in virtual space 122 may be spatially arranged such that a message thread having an associated electronic message that was sent more recently is depicted closer to a virtual instance of the accessing user in the virtual space 133, than each message thread for which an electronic message was sent less recently. In some examples, an avatar corresponding to the sender of each electronic message in an electronic messaging thread may be depicted in the virtual space 122. Each avatars may be spatially arranged for an electronic messaging thread such that a message of an electronic messaging thread that was sent more recently, will have a corresponding sender avatar that is depicted closer to a virtual instance of a requesting user in virtual space 122, than a sender avatar corresponding to an electronic message of the electronic messaging thread that was sent less recently. In some examples, sender avatars may be spatially arranged in a linear fashion, with sender avatars corresponding to most recent and/or most relevant messages being most proximate to a virtual instance of a requesting user in virtual space 122. In other examples, sender avatars may be spatially arranged in other formats reflecting the time of sending of corresponding messages (e.g., a clockwise spatial arrangement, a counter-clockwise spatial arrangement). In such arrangements, for example, upon interacting with a first, most recent and/or relevant message, the next sender avatar and corresponding message may be visually represented in the virtual space 122 by the next sender avatar in a cluster in a clockwise or counter-clockwise direction in the cluster. Other clustering mechanisms reflecting a time that electronic messages were sent and/or the relevance of electronic messages represented in the virtual space 122 may also be utilized.

In some examples, each sender avatar depicted in the virtual space 122 may be displayed in association with at least a portion of an electronic message of an electronic messaging thread that the sending user associated with that avatar sent to the accessing user 104B. In other examples, only a first sender avatar in the virtual space, which is depicted closest to a virtual instance of the accessing user 104B in the virtual space 122 may be displayed in association with at least a portion of an electronic message of an electronic messaging thread that the sending user associated with that avatar sent to the accessing user 104B (as is the case in the illustrated virtual space 122). In still other examples, only sender avatars depicted in the virtual space 122, for which a virtual instance of the accessing user 104B has reached a virtual threshold distance in the virtual space 122, may be depicted with at least a portion of an electronic message of an electronic messaging thread that the sending user associated with that avatar sent to the accessing user 104B. For example, as a virtual instance of user 104B approaches a first sender avatar in the virtual space 122, at least a portion of an electronic message that a messaging user associated with that sender avatar sent may be displayed in the virtual space 122 approximate that sender avatar when the virtual instance of accessing user 104B reaches a threshold distance within the virtual space 122 of the sender avatar.

An accessing user, such as user 104A and user 104B may traverse the virtual space 122 via one or more input mechanisms. For example, an accessing user may move (e.g., modify a virtual point of view) the accessing user's virtual instance in relation to other objects (e.g., sender avatars, electronic messages, electronic message threads, etc.) in the virtual space by sending movement inputs from a client computing device (e.g., virtual reality computing devices 106A and 106B) to a virtual messaging service in messaging service and processing environment 116. Thus, an accessing user's physical movements may be captured by a corresponding accessing client computing device and allow a user's physical movements to be mirrored within a virtual space. In some examples, rather than mirroring physical movements (e.g., steps, head movements, etc.) in a virtual space of a virtual messaging application based on physical movement inputs received from an accessing user's client computing device, an accessing user may traverse a virtual space by utilizing one or more input devices (e.g., a keyboard, a joystick, a mouse, a controller, etc.) connected to the accessing client computing device in order to traverse the virtual space. In still other examples, spoken commands received by a client computing device and an associated virtual messaging application may be utilized to allow an accessing user to traverse a virtual space of a virtual messaging application.

In examples, user 104B may virtually interact with one or more messages and/or associated avatars in the virtual space 122 via virtual reality computing device 106B. For example, accessing user 104B may issue a command, via virtual reality computing device 106B, to have a sender avatar read an electronic message that a corresponding sending user sent to user 104B. That command may be sent, via network 114, to a virtual messaging service in messaging service and processing environment 116, and one or more computing devices in messaging service and processing environment 116 may cause the sender avatar to read the electronic message aloud in virtual space 122 (e.g., via speakers associated with virtual reality computing device 106B). In other examples, the processing of such a command may be handled independently by virtual reality computing device 106B (i.e., sending of that command to a virtual messaging service is not necessary in some examples).

User 104B may interact with one or more electronic messages and/or corresponding avatars utilizing other mechanisms. For example, user 104B may utilize a gesture mechanism which may be captured via a camera associated with virtual reality computing device 106B, or a different type of hardware input device associated with virtual reality computing device 106B, in order to view an attachment associated with a message depicted or otherwise represented in virtual space 122, delete a message depicted or otherwise represented in virtual space 122, read an entire message depicted or otherwise represented in virtual space 122, open a text messaging dialog between the accessing user 104B and a sender of a message depicted or otherwise represented in virtual space 122, open an audio messaging dialog between the accessing user 104B and a sender of a message depicted or otherwise represented in virtual space 122, and/or open a video messaging dialog between the accessing user 104B and a sender of a message depicted or otherwise represented in the virtual space.

In some examples, in opening a communication dialog between user 104B and a sending user of a message depicted or otherwise represented in virtual space 122, the dialog may be represented within virtual space 122. For example, if an audio messaging dialog is initiated, a sender avatar corresponding to the sending user of a message that the accessing user 104B initiates the dialog with may be caused to be displayed as speaking to the virtual instance of accessing user 104B in the virtual space 122 during that dialog. Likewise, if a text messaging dialog is initiated, a sender avatar corresponding to the sending user of a message that the accessing user 104B initiates the dialog with may be shown in association with text that is typed by that avatar during the text messaging dialog within the virtual space 122. Similarly, if a video messaging dialog is initiated, a sender avatar corresponding to the sending user of a message that the accessing user 104B initiates the dialog with may be shown in association with a video window in the virtual space 122 depicting the sending user's video environment in the virtual space.

Figure 2:
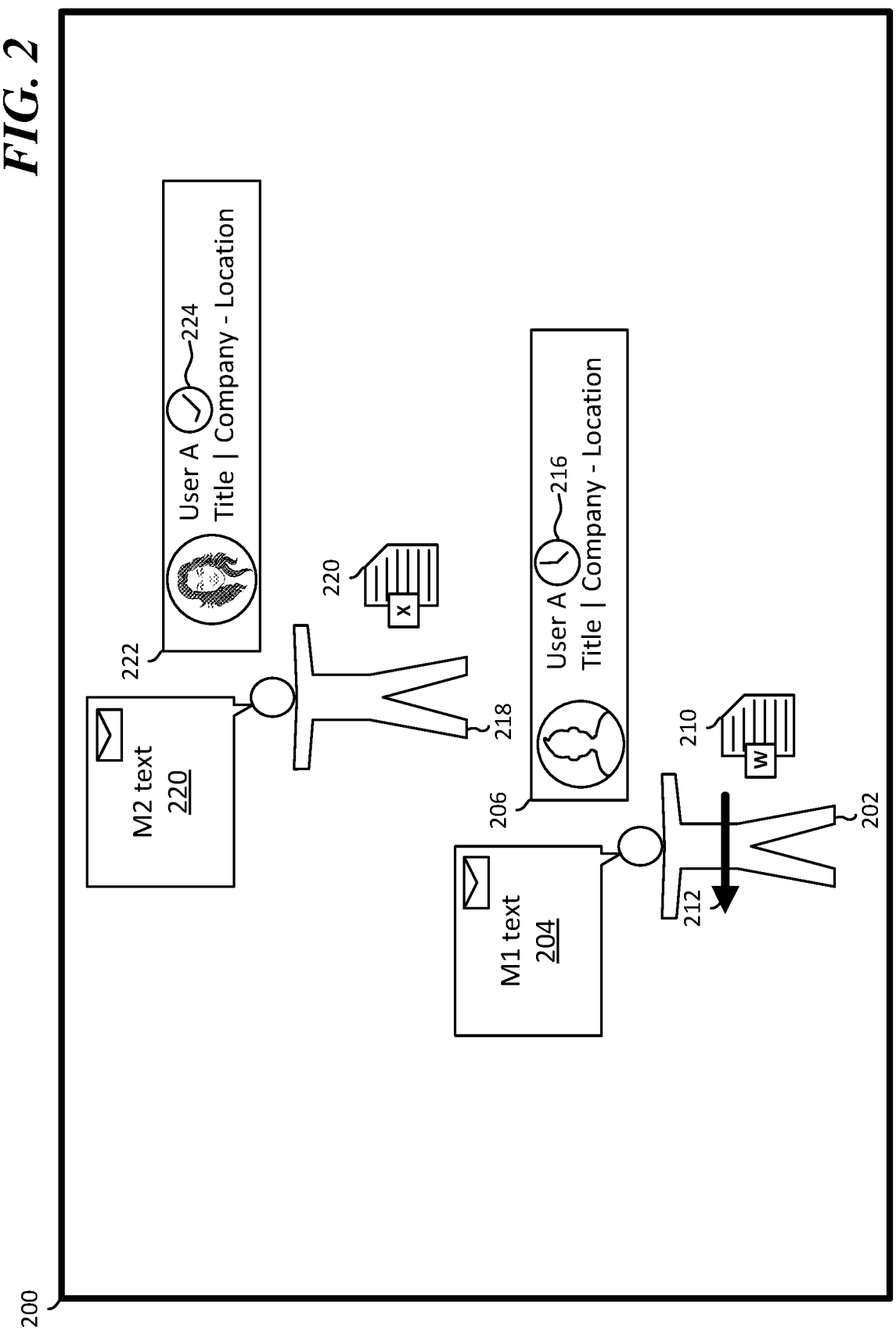
FIG. 2 illustrates an exemplary user interface for virtually interacting with a plurality of electronic messages and their corresponding sender avatars presented in a virtual space.
Figure 3:
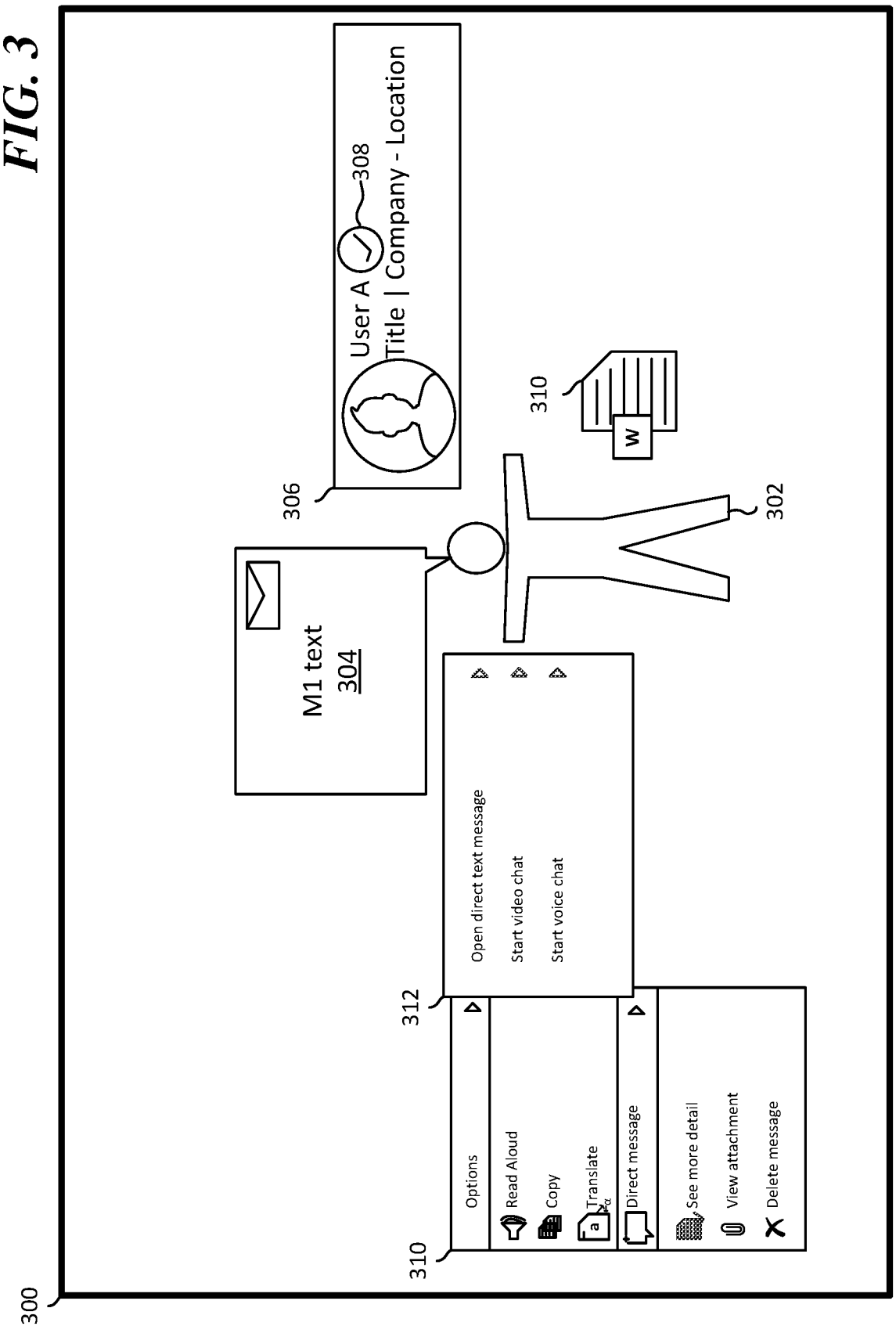
FIG. 3 illustrates an exemplary user interface for executing one or more actions in a virtual space associated with an electronic message and its associated sender.

In additional examples, a sender avatar depicted in virtual space 122 may be displayed in virtual space 122 in association with contact details for a sending user associated with that sender avatar. In examples, the contact information may be retrieved from one or more social network services associated with an account of the sending user. Thus, in the illustrated example, server computing device 120 may request that contact information associated with a sender of one or more messages depicted in association with one or more avatars in virtual space 122, be obtained from one or more social network service account databases, such as social network service account database 112. That is a social network account associated with one or more electronic message senders (and corresponding avatars) may be accessed and information about the one or more message senders may be sent from the social network database associated with the social network account to a virtual messaging service in messaging service and processing environment 116, and one or more computing devices in messaging service and processing environment 116 may cause that information to be displayed in virtual space 122 in association with (e.g., adjacent to, overlapping with) a corresponding avatar. FIG. 2 and FIG. 3 and their corresponding descriptions herein provide additional detail regarding the information that may be obtained from a social network service for an electronic message sender and caused to be displayed in virtual space 122 of a virtual messaging application in association with a corresponding sender avatar.

FIG. 2 illustrates an exemplary user interface 200 for virtually interacting with a plurality of electronic messages and their corresponding sender avatars presented in a virtual space. The exemplary user interface 200 depicts a virtual space displayed on a client computing device. The client computing device may comprise a virtual reality computing device, an augmented reality computing device, or a mixed reality computing device. The virtual space of exemplary user interface 200 includes a first sender avatar 202 and a second sender avatar 218. In examples, the first sender avatar 202 may correspond to a sending user of an electronic message that was sent to an account associated with an accessing user at a time that is more recent than an electronic message sent to the accessing user which corresponds to the second sender avatar 218. Thus, in this example, the first sender avatar 202 is depicted closer in the virtual space to a virtual instance of the accessing user than the second sender avatar 218.

The accessing user may interact with an electronic message corresponding to the first sender avatar 202 via one or more inputs into the client computing device (e.g., a virtual reality computing device, an augmented reality computing device, a mixed reality computing device), including a spoken input, a gesture input, and/or a hardware input associated with the client computing device. In this example, exemplary user interface 200 includes a display of at least a portion of an electronic message 204 sent from a sending user of the electronic message associated with the first sender avatar 202, information 206 associated with the sending user, a visual indication of an attachment 210 that was included in the electronic message that was sent by the sending user corresponding to the first sender avatar 202, as well as an indication 212 that the accessing user may delete the electronic message that was sent by the sending user corresponding to the first sender avatar 202. The accessing user may delete the electronic message by, for example, inputting a "swipe left" gesture into the client computing device. In some examples, a command to delete the electronic message may delete the electronic message and the corresponding sender avatar from the virtual space of the virtual messaging application. In other examples, the command to delete the electronic message may delete an instance of the electronic message from storage associated with the virtual messaging service. In still other examples, the command to delete the electronic message may delete the electronic message from the electronic messaging service from which it was originally retrieved.

The information 206 associated with the sending user may include information corresponding to the sending user, such as the name of the sending user, the title of the sending user, a company name associated with the sending user, and a geographic location of the sending user (e.g., a current geographic location of the sending user, a residence geographic location of the sending user, a geolocation of a company that the sending user is affiliated with, etc.). The information 206 associated with the sending user may be obtained by a virtual messaging service from one or more social network applications that the sending user is associated with. For example, one or more computing devices associated with the messaging service may send an email address or other identifier of the sending user obtained from the corresponding electronic message to a social network service or social network service database, and request one or more pieces of information that are to be included in the information 206 associated with the sending user in the virtual space illustrated in exemplary user interface 200.

In some examples, the information 206 associated with the sending user may include a presence indication 216 of whether the sending user is available at a computing device. In the illustrated example, the presence indication 216 of whether the sending user is available at a computing device may comprise a clock element, which may be displayed in a color corresponding to the status of the user. For example, the presence indication 216 may be displayed on exemplary user interface 200 in a green color if the sending user is currently available (e.g., available for starting a text, audio, or video chat with, active at a computing device) at a computing device. In other examples, the presence indication 216 may be displayed on exemplary user interface 200 in a yellow color if the sending user is currently idle at a computing device. In still other examples, the presence indication 216 may be displayed on exemplary user interface 200 in a red color if the sending user is currently busy at a computing device. Other user interface elements are possible for indicating whether the sending user is available or unavailable at a computing device. For example, a check mark may be indicated in the presence indication 216 if a user is currently available at computing device. In additional examples, a color of a sender avatar may indicate the presence of a sending user corresponding to that user in the virtual space of a virtual messaging application.

The accessing user may virtually interact with the electronic message corresponding to first sender avatar 202 by for example, indicating via the accessing user's client computing device, that the accessing user would like to have one or more actions taken associated with the electronic message, the first sending avatar 202, and/or an attachment 210 of the electronic message. In examples, the accessing user may provide a voice input to the client computing device in order to interact with the electronic message and/or the sending first sender avatar 202. In other examples, the accessing user may provide a gesture input to the client computing device in order to interact with electronic message and/or the first sender avatar 202. In still other examples the client computing device may be physically or wirelessly connected to an input device, such as a mouse, a controller, a keyboard, etc., and one or more indications may be provided via the physically or wirelessly connected input device in order for the accessing user to indicate that one or more actions associated with the electronic message and/or the first sender avatar 202 should be executed.

The accessing user may navigate a virtual instance of the accessing user (e.g., a point of view of the accessing user in the virtual space, a third-person view of the accessing user in the virtual space) by one or more input mechanisms to the client computing device. For example, the client computing device may have motion sensors that detect the accessing user's physical movements in the real world and those movements may be mirrored within the virtual space. Thus, if a user walks forward in the real world while holding, wearing, or otherwise moving the client computing device in a forward direction, the virtual instance of the user in the virtual space may similarly move forward. In example where a virtual reality computing device is being worn on the head of the accessing user, motion sensors in the virtual reality computing device may detect head movements of the accessing user and mirror those movements within the virtual space. Thus, if an accessing user moves her head left, right, up, or down, those movements may be detected by the virtual reality computing device, and the virtual instance view in the virtual space may mirror those changes in the user interface.

In some examples, the accessing user may interact (e.g., perform one or more executable actions) with either a sender avatar, such as first sender avatar 202 or second sender avatar 218 and/or a corresponding electronic message at any virtual distance between the sender avatar and a virtual instance of the accessing user in the virtual space. In other examples, the accessing user's virtual instance may need to be within a threshold virtual distance of a sender avatar in order to interact with a sender avatar and/or corresponding electronic message.

In some examples, a sender avatar associated with an electronic message may be displayed without additional information (e.g., information associated with a corresponding sending user, information associated with a corresponding electronic message) within the virtual space if a virtual instance of an accessing user is not within a virtual threshold distance of the sender avatar in the virtual space. Thus, additional information associated with the second sender avatar, including as at least a portion of an electronic message 220 corresponding to the second sender avatar 218, information 222 associated with the second sending user, a presence indication 224, a visual indication of an attachment 220 that was included in the electronic message that was sent by the sending user corresponding to the second sender avatar 218, and/or an indication that the accessing user may delete the electronic message that was sent by the sending user corresponding to the second sender avatar 218, may only be caused to be displayed in the virtual space depicted by the exemplary user interface 200 upon the accessing user virtually navigating the accessing user's virtual instance within a virtual threshold distance of the second sender avatar.

In some examples, the sender avatar may be displayed within the virtual space with one or more pieces of additional information regardless of the virtual distance between the sender avatar and a virtual instance of an accessing user. In other examples, a first one or more pieces of additional information may be displayed in association with a sender avatar based on a virtual instance of an accessing user being within a first virtual threshold distance of the sending avatar, and a second one or more pieces of additional information may be displayed in association with a sender avatar when a virtual instance of an accessing user is determined to be within a second virtual threshold distance of the sender avatar. Thus, as a virtual instance of an accessing user moves closer to a sender avatar in a virtual space, additional pieces of information associated with that avatar, a sending user associated with that avatar, and/or a corresponding electronic message, may be caused to be displayed in an area associated with the sender avatar at various virtual threshold distances during the virtual instance of the accessing user's approach. Similarly, as a virtual instance of an accessing user moves away from a sending avatar in a virtual space, additional pieces of information associated with that avatar, a sending user associated with that avatar, and/or a corresponding message, may be caused to no longer be displayed in an area associated with the sender avatar at various threshold distances during the virtual instance of the accessing user's distancing from the sender avatar in a virtual space.

FIG. 3 illustrates an exemplary user interface 300 for executing one or more actions in a virtual space associated with an electronic message and its associated sender. The exemplary user interface 300 comprises a sender avatar 302 associated with a corresponding electronic message sent to an electronic messaging account associated with an accessing user, at least a portion of the corresponding electronic message 304 sent from a sending user of the corresponding electronic message associated with the sender avatar 302, information 306 associated with the sending user, a presence indication 308 for the sending user of the corresponding electronic message, a visual indication of an attachment 310 that was included in the corresponding electronic message that was sent by the sending user corresponding to the sender avatar 302, selectable option pop-up menu 310, and fly-out menu 312.

In examples, the selectable option pop-up menu 310 associated with the sender avatar and a corresponding electronic message, may be included in the virtual space depicted in exemplary user interface 300 upon a virtual instance of the accessing user being determined to be within a threshold distance of the sender avatar 302 within the virtual space. In other examples, the selectable option pop-up menu 310 associated with the sender avatar may be caused to be displayed when the accessing user indicates via the accessing user's client computing device (e.g., a virtual reality computing device, an augmented reality computing device), that the accessing user would like to have the pop-up menu 310 displayed within the virtual space in association with the sender avatar 302. In examples, the indication may comprise a spoken indication received by the accessing user's client computing device, a gesture indication received by the accessing user's client computing device, or an input from a hardware input component connected (e.g., wired or wireless connection) to the accessing user's client computing device.

The pop-up menu 310 comprises a plurality of selectable executable actions that may be performed on the corresponding electronic message, in association with the corresponding electronic message, on the sender avatar 302, and/or an attachment sent with the corresponding electronic message. In this example, the executable options shown in pop-up menu comprise: a "read aloud" option (e.g., an option to have at least a portion of text included in the corresponding electronic message read aloud by the accessing user's client computing device and/or by the sender avatar in the virtual space), a "copy" option (e.g., an option to copy at least a portion of text included in the corresponding electronic message), a "translate" option (e.g., an option to have at least a portion of text included in the corresponding electronic message translated from its original language into one or more additional languages), a "direct message" option (e.g., an option to initiate a text, audio, and/or video dialog within the virtual space), a "see more detail" option (e.g., an option to view more information associated with the corresponding electronic message, such as a time that the electronic message was sent, an email address of the sender of the electronic message, a size of the electronic message, etc.), a "view attachment" option (e.g., an option to view an attachment included with the corresponding electronic message within the virtual space), and a "delete message" option (e.g., an option to delete the corresponding electronic message and/or have the electronic message and its corresponding sender avatar 302 removed from the virtual space).

In the illustrated example, an accessing user has indicated (e.g., via the "direct message" option) that the accessing user would like to initiate a direct message with a sending user associated with the sender avatar and the corresponding electronic message, and upon so indicating, the fly-out menu 312 for that option has been caused to be displayed. The fly-out menu 312 for the "direct message" option comprises selectable options to initiate one or more of: a direct text message dialog between the accessing user and a sending user associated with the sender avatar 302, a video chat dialog between the accessing user and a sending user associated with the sender avatar 302, and a voice chat dialog between the accessing user and a sending user associated with the sender avatar 302. In some examples, upon the accessing user indicating, via the accessing user's client computing device, that the accessing user would like to initiate a direct message with a sending user associated with the sender avatar 302, the indicated messaging dialog may be initiated from within the virtual space of exemplary user interface 300.

In examples, if the "open direct text message" option is selected, a text box for communicating directly with the user associated with the sender avatar 302 may be caused to be displayed in association with the sender avatar 302 within the virtual space. Likewise, if the "start video chat" option is selected, a video window for communicating via video with the user associated with the sender avatar 302 may be caused to be displayed in association with the sender avatar 302 within the virtual space. Similarly, if the "start voice chat" option is selected, audio communications (e.g., VoIP) may be initiated between the accessing user's client computing device and a computing device associated with a user associated with the sender avatar 302. In some examples, when the "start voice chat" option is selected, and audio communications have been initiated, the sender avatar 302 may be caused to mirror physical talking characteristics of a user when voice audio is received from the user associated with the sender avatar 302 during the voice chat. In still other examples, one or more communication applications separate from the virtual messaging application, which may be installed or otherwise accessed via the accessing user's client computing device, may be initiated and utilized to communicate with a user associated with the sender avatar 302 when one or more of the "direct message" options have been selected by the accessing user.

In some examples, the options presented by one or both of selectable option pop-up menu 310, and fly-out menu 312 may be presented to an accessing user in an audio or text format, rather than the displayed menu format shown in FIG. 3. For example, an accessing user may be provided with one or more options corresponding to pop-up menu 310 and/or fly-out menu 312 via interacting with a virtual digital assistant (e.g., Cortana, Siri, etc.) that is integrated with the virtual messaging application and/or the virtual messaging service described herein.

Figure 4:
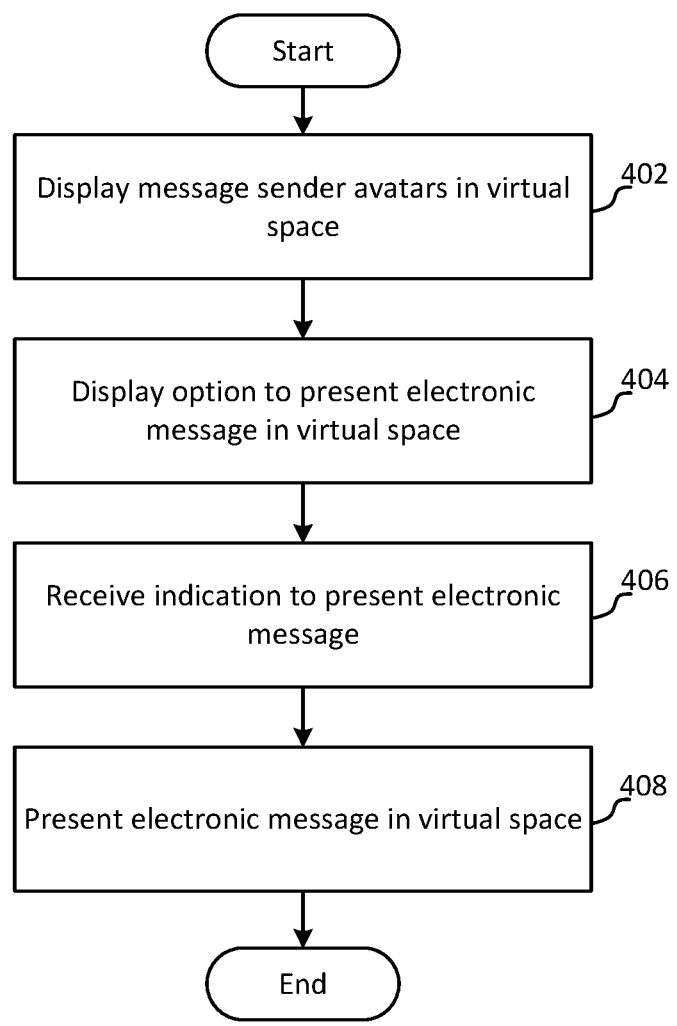
FIG. 4 is an exemplary method interacting with one or more electronic messages in a virtual space provided by a client computing device.

FIG. 4 is an exemplary method 400 interacting with one or more electronic messages in a virtual space provided by a client computing device. The method 400 begins at a start operation and flow continues to operation 402.

At operation 402 a sender avatar associated with an electronic message sent to a messaging account of an accessing user is displayed in a virtual space of a virtual messaging user interface of a client computing device. The client computing device may comprise a virtual reality computing device, an augmented reality computing device and/or a mixed reality computing device.

From operation 402 flow continues to operation 404 where an option is displayed in association with the sender avatar within the virtual space to present a corresponding electronic message in the virtual space. In some examples, the option may be caused to be displayed when a virtual instance of an accessing user is determined to be within a virtual threshold distance of the sender avatar. In other examples, the option may be caused to be displayed when the sender avatar is within view of the virtual instance of the accessing user in the virtual space. In still other examples, the option may be caused to be displayed upon the accessing user indicating, via the client computing device, that the accessing user would like to have the option displayed in the virtual space.

From operation 404 flow continues to operation 406 where an indication to present at least a portion of the electronic message in the virtual space is received. In some examples, the indication may comprise a voice input by the accessing user to the client computing device. In other examples, the indication may comprise a gesture input by the accessing user to the client computing device. In still other examples, the indication may comprise an indication received via a device input connected (e.g., an input device connected wirelessly, an input device with a wired connection) to the client computing device.

From operation 406 flow continues to operation 408 where the electronic message associated with the sender avatar is presented in the virtual space in association with the sender avatar. In examples, at least a portion of text of the electronic message may be read audibly by the sender avatar in the virtual space. In other examples, at least a portion of the message may be displayed within the virtual space. In still other examples, an application separate from the virtual messaging application may be accessed by the client computing device and the electronic message may be opened via that application and caused to be displayed in that separate application.

From operation 408 flow continues to an end operation, and the method 400 ends.

Figure 5:
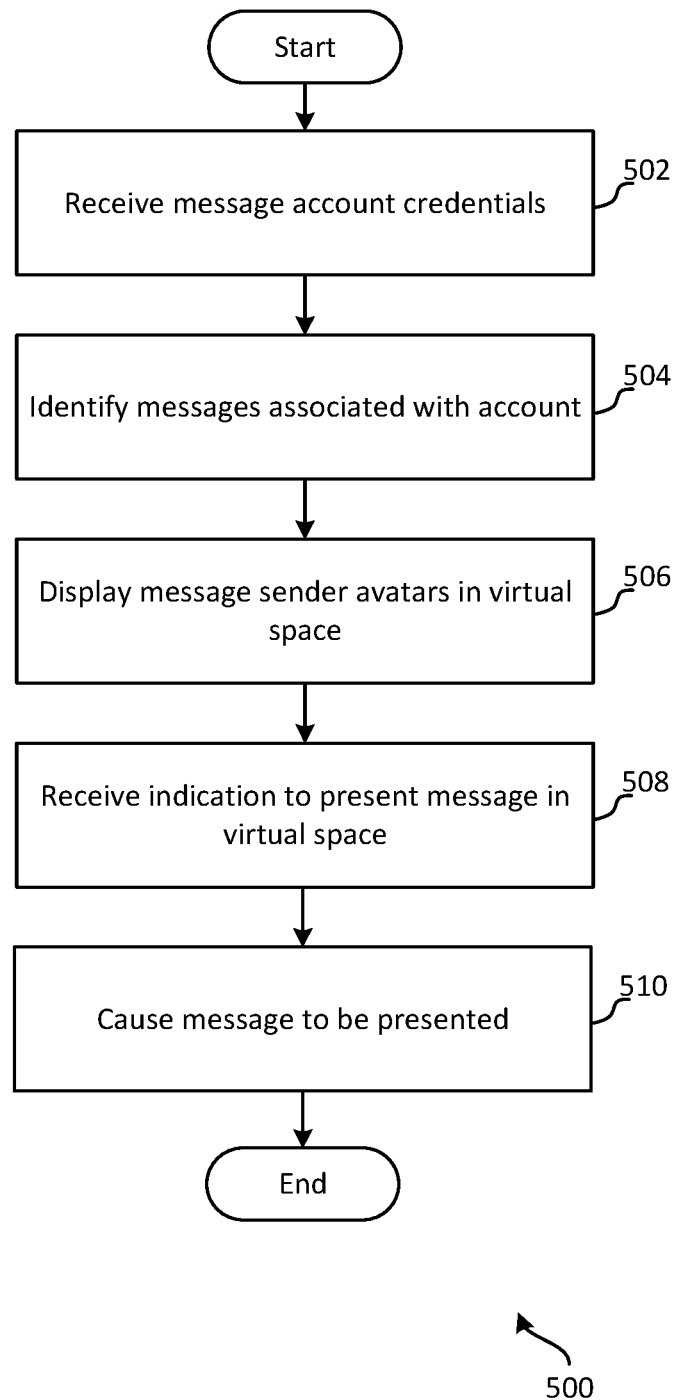
FIG. 5 is an exemplary method for assisting with interacting with one or more electronic messages in a virtual space of a client computing device.

FIG. 5 is an exemplary method 500 for assisting with interacting with one or more electronic messages in a virtual space of a client computing device. The method 500 begins at a start operation and flow moves to operation 502.

At operation 502 credentials of an accessing user associated with one or more electronic messaging services are received. For example, a user may access a virtual messaging application from a client computing device (e.g., a virtual reality computing device, an augmented reality computing device, a mixed reality computing device), and input the user's credentials for accessing one or more messaging applications (e.g., an email application, an SMS messaging application, etc.). The user's credentials may then be sent to a virtual messaging service as described more fully with regard to FIG. 1.

From operation 502 flow continues to operation 502 where one or more electronic messages associated with the received credentials are identified. In some examples, in identifying the one more electronic messages associated with the received credentials, the virtual messaging service may communicate with one or more messaging services that the received credentials are associated with. For example, the virtual messaging service may send the received credentials to an email application service and request that one or more messages associated with an account to which access may be granted via the credentials be sent to the virtual messaging service from the email application service. In some examples, all messages from the electronic messaging service may be sent to the virtual messaging service upon the electronic messaging service receiving the request. In additional examples, a push mechanism may be utilized such that upon each new electronic message associated with the credentialed account being received by the electronic messaging service, the new electronic messages are sent to the virtual messaging service. In other examples, a pull mechanism may be utilized by the virtual messaging service. For example, the virtual messaging service may store received credentials from an accessing user, and periodic requests including those credentials may be sent from the virtual messaging service to one or more electronic messaging services to retrieve any new messages associated with a credentialed account from the one or more electronic messaging services.

From operation 504 flow continues to operation 506 where one or more sender avatars associated with one or more of the identified messages are caused to be displayed in a virtual space of a virtual messaging application of the client computing device of the accessing user. In some examples, a sender avatar corresponding to a sending user of each identified message may be caused to be displayed in the virtual space. In other examples, a subset of avatars corresponding to a sending user of a subset of the identified messages may be caused to be displayed in the virtual space. For example, a subset of sender avatars corresponding to the most recently sent identified messages may be caused to be displayed in the virtual space. In another example, an accessing user may perform a search using key words or phrases for a subset of identified messages relevant to the search, and one or more most relevant sender avatars corresponding to the most relevant identified messages based on that search may be caused to be displayed in the virtual space. In additional examples, the displayed sender avatars may be spatially arranged in the virtual space based on a time that each corresponding message was sent to an electronic messaging account associated with the accessing user's credentials. In some examples, the more recently an identified message was sent to a messaging account of the accessing user, the closer a corresponding sender avatar will be presented in the virtual space in relation to a virtual instance of the accessing user.

From operation 506 flow continues to operation 508 where an indication to present an electronic message corresponding to a displayed sender avatar is received. In some examples, the indication may comprise a spoken request from the accessing user sent from the accessing user's client computing device to the virtual messaging service. In other examples, the indication may comprise a gesture request received from the accessing user by the client computing device and sent to the virtual messaging service. In still other examples, an input device connected to the accessing user's client computing device may be utilized to send an indication to present a message in the virtual space to the virtual messaging service. In additional examples, the indication may specify one or more mechanisms for presenting the electronic message in the virtual space. Thus, the indication may comprise a request to have the message audibly read in the virtual space by a corresponding sender avatar, a request to display at least a portion of the message in association with a corresponding sender avatar in the virtual space, and/or a request to open an application separate from the virtual messaging application on the client computing device for opening the electronic message and displaying and/or audibly communicating the electronic message via the accessing user's client computing device.

From operation 508 flow continues to operation 510 where the electronic message is caused to be presented to the accessing user by the client computing device. In examples, the electronic message may be presented in a requested format as discussed in relation to operation 508. For example, at least a portion of the electronic message may be read audibly by a corresponding sender avatar, at least a portion of the electronic message may be caused to be displayed in association with a corresponding sender avatar, and/or an application separate from the virtual messaging application may be caused to open the electronic message and present it from the accessing user's client computing device.

From operation 510 flow continues to an end operation, and the method 500 ends.

Figure 6:
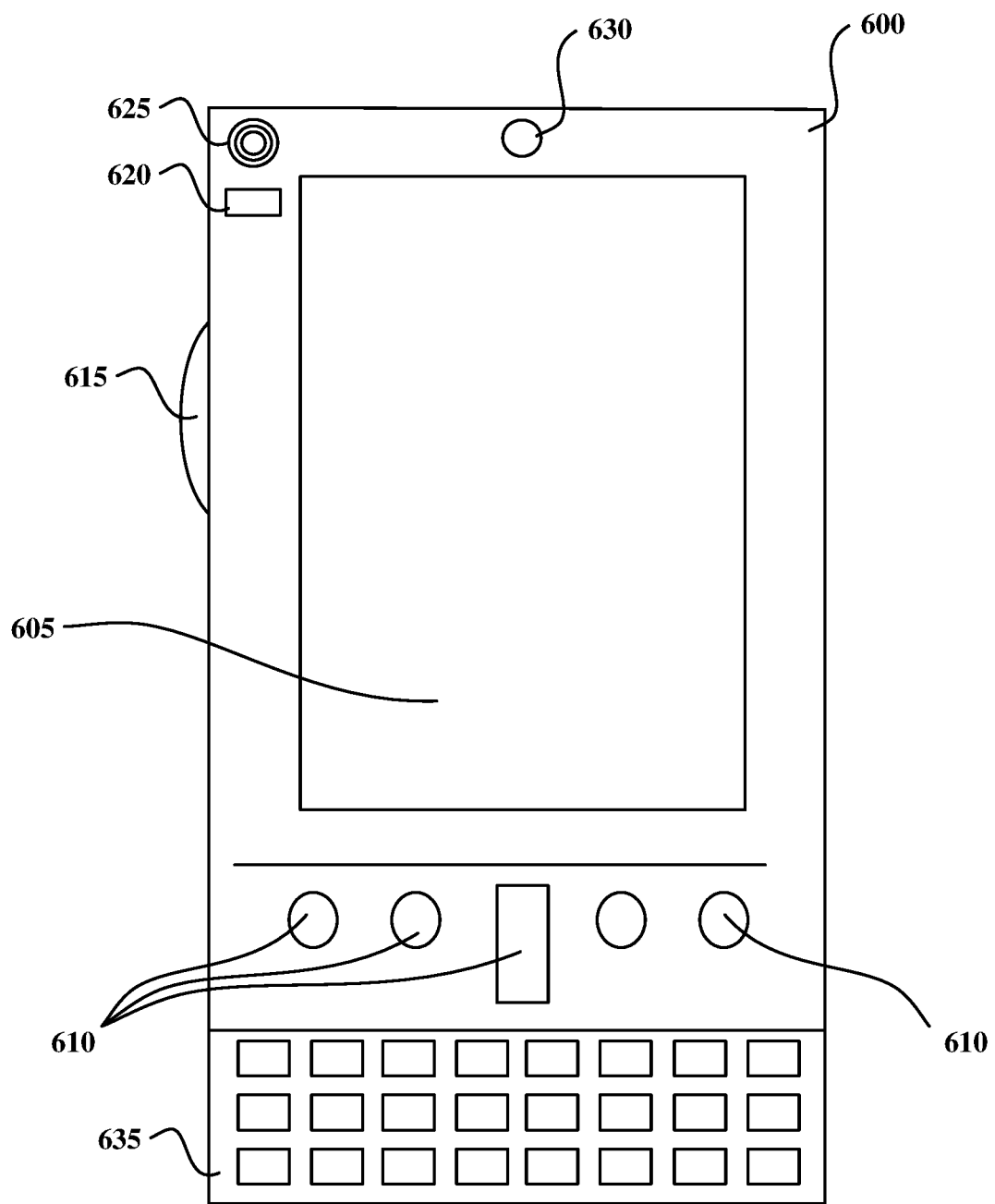
FIGS. 6 and 7 are simplified diagrams of a mobile computing device with which aspects of the disclosure may be practiced.
Figure 7:
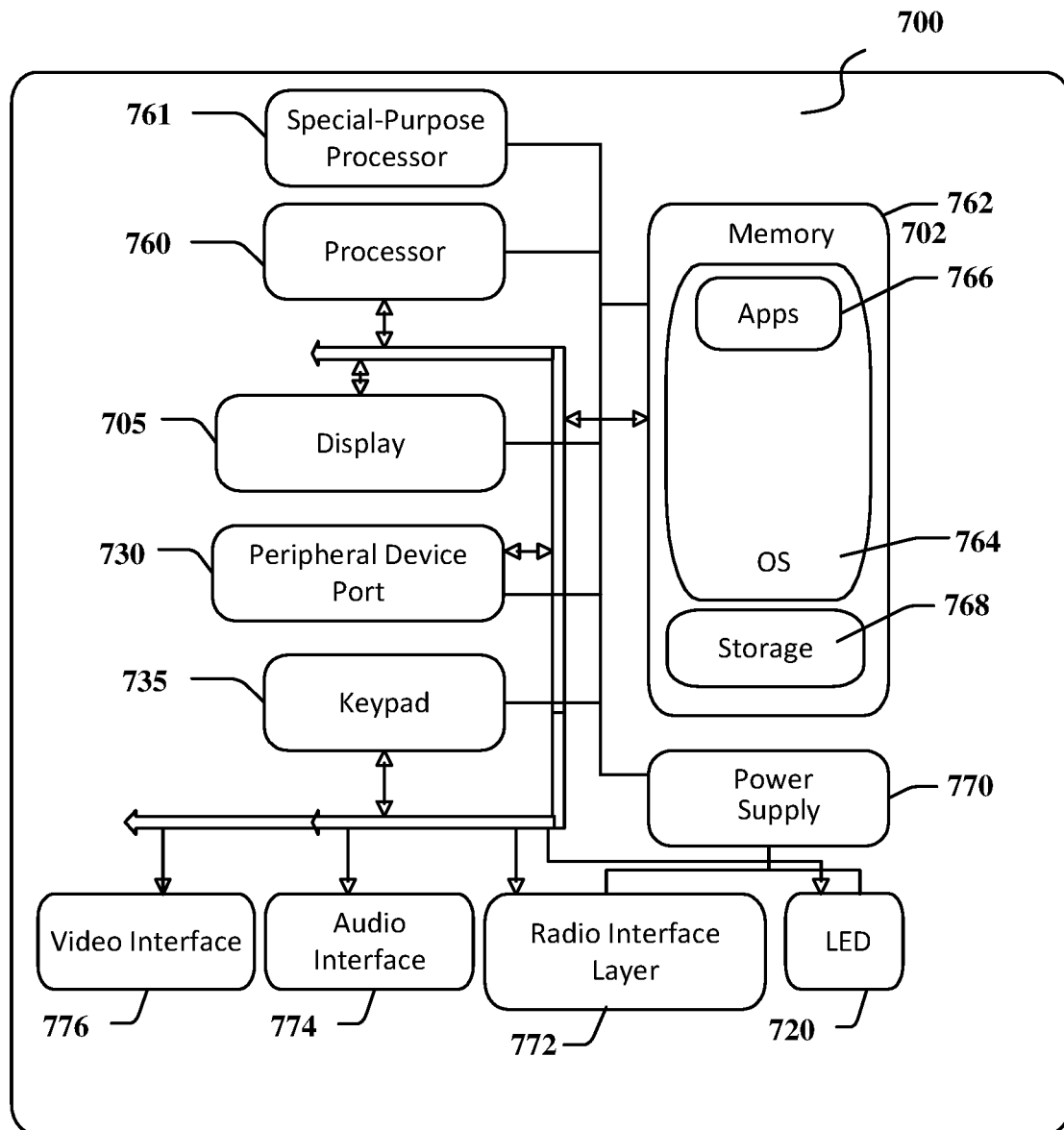

FIGS. 6 and 7 illustrate a mobile computing device 600, for example, a mobile telephone, a smart phone, wearable computer (e.g., a virtual reality computing device, an augmented reality computing device, a mixed reality computing device), a tablet computer, an e-reader, a laptop computer, or other AR or VR compatible computing device, with which embodiments of the disclosure may be practiced. With reference to FIG. 6, one aspect of a mobile computing device 600 for implementing the aspects is illustrated. In a basic configuration, the mobile computing device 600 is a handheld computer having both input elements and output elements. The mobile computing device 600 typically includes a display 605 and one or more input buttons 610 that allow the user to enter information into the mobile computing device 600. The display 605 of the mobile computing device 600 may also function as an input device (e.g., a touch screen display). If included, an optional side input element 615 allows further user input. The side input element 615 may be a rotary switch, a button, or any other type of manual input element. In alternative aspects, mobile computing device 600 may incorporate more or fewer input elements. For example, the display 605 may not be a touch screen in some embodiments. In yet another alternative embodiment, the mobile computing device 600 is a portable phone system, such as a cellular phone. The mobile computing device 600 may also include an optional keypad 635. Optional keypad 635 may be a physical keypad or a "soft" keypad generated on the touch screen display. In various embodiments, the output elements include the display 605 for showing a graphical user interface (GUI), a visual indicator 620 (e.g., a light emitting diode), and/or an audio transducer 625 (e.g., a speaker). In some aspects, the mobile computing device 600 incorporates a vibration transducer for providing the user with tactile feedback. In yet another aspect, the mobile computing device 600 incorporates input and/or output ports, such as an audio input (e.g., a microphone jack), an audio output (e.g., a headphone jack), and a video output (e.g., a HDMI port) for sending signals to or receiving signals from an external device.

FIG. 7 is a block diagram illustrating the architecture of one aspect of a mobile computing device. That is, the mobile computing device 700 can incorporate a system (e.g., an architecture) 702 to implement some aspects. In one embodiment, the system 702 is implemented as a "smart phone" capable of running one or more applications (e.g., browser, e-mail, calendaring, contact managers, messaging clients, games, and media clients/players). In some aspects, the system 702 is integrated as a computing device, such as an integrated personal digital assistant (PDA) and wireless phone.

One or more application programs 766 may be loaded into the memory 762 and run on or in association with the operating system 864. Examples of the application programs include phone dialer programs, e-mail programs, personal information management (PIM) programs, word processing programs, spreadsheet programs, Internet browser programs, messaging programs, and so forth. The system 702 also includes a non-volatile storage area 768 within the memory 762. The non-volatile storage area 768 may be used to store persistent information that should not be lost if the system 702 is powered down. The application programs 766 may use and store information in the non-volatile storage area 768, such as e-mail or other messages used by an e-mail application, and the like. A synchronization application (not shown) also resides on the system 702 and is programmed to interact with a corresponding synchronization application resident on a host computer to keep the information stored in the non-volatile storage area 768 synchronized with corresponding information stored at the host computer. As should be appreciated, other applications may be loaded into the memory 762 and run on the mobile computing device 700, including instructions for providing and operating a virtual messaging computing platform.

The system 702 has a power supply 770, which may be implemented as one or more batteries. The power supply 770 might further include an external power source, such as an AC adapter or a powered docking cradle that supplements or recharges the batteries.

The system 702 may also include a radio interface layer 772 that performs the function of transmitting and receiving radio frequency communications. The radio interface layer 772 facilitates wireless connectivity between the system 702 and the "outside world," via a communications carrier or service provider. Transmissions to and from the radio interface layer 772 are conducted under control of the operating system 764. In other words, communications received by the radio interface layer 772 may be disseminated to the application programs 766 via the operating system 764, and vice versa.

The visual indicator 620 may be used to provide visual notifications, and/or an audio interface 774 may be used for producing audible notifications via the audio transducer 625. In the illustrated embodiment, the visual indicator 620 is a light emitting diode (LED) and the audio transducer 625 is a speaker. These devices may be directly coupled to the power supply 770 so that when activated, they remain on for a duration dictated by the notification mechanism even though the processor 760 and other components might shut down for conserving battery power. The LED may be programmed to remain on indefinitely until the user takes action to indicate the powered-on status of the device. The audio interface 774 is used to provide audible signals to and receive audible signals from the user. For example, in addition to being coupled to the audio transducer 625, the audio interface 774 may also be coupled to a microphone to receive audible input, such as to facilitate a telephone conversation. In accordance with embodiments of the present disclosure, the microphone may also serve as an audio sensor to facilitate control of notifications, as will be described below. The system 702 may further include a video interface 776 that enables an operation of an on-board camera 630 to record still images, video stream, and the like.

A mobile computing device 700 implementing the system 702 may have additional features or functionality. For example, the mobile computing device 700 may also include additional data storage devices (removable and/or non-removable) such as, magnetic disks, optical disks, or tape. Such additional storage is illustrated in FIG. 7 by the non-volatile storage area 768.

Data/information generated or captured by the mobile computing device 700 and stored via the system 702 may be stored locally on the mobile computing device 700, as described above, or the data may be stored on any number of storage media that may be accessed by the device via the radio interface layer 772 or via a wired connection between the mobile computing device 700 and a separate computing device associated with the mobile computing device 700, for example, a server computer in a distributed computing network, such as the Internet. As should be appreciated such data/information may be accessed via the mobile computing device 700 via the radio interface layer 772 or via a distributed computing network. Similarly, such data/information may be readily transferred between computing devices for storage and use according to well-known data/information transfer and storage means, including electronic mail and collaborative data/information sharing systems.

Figure 8:
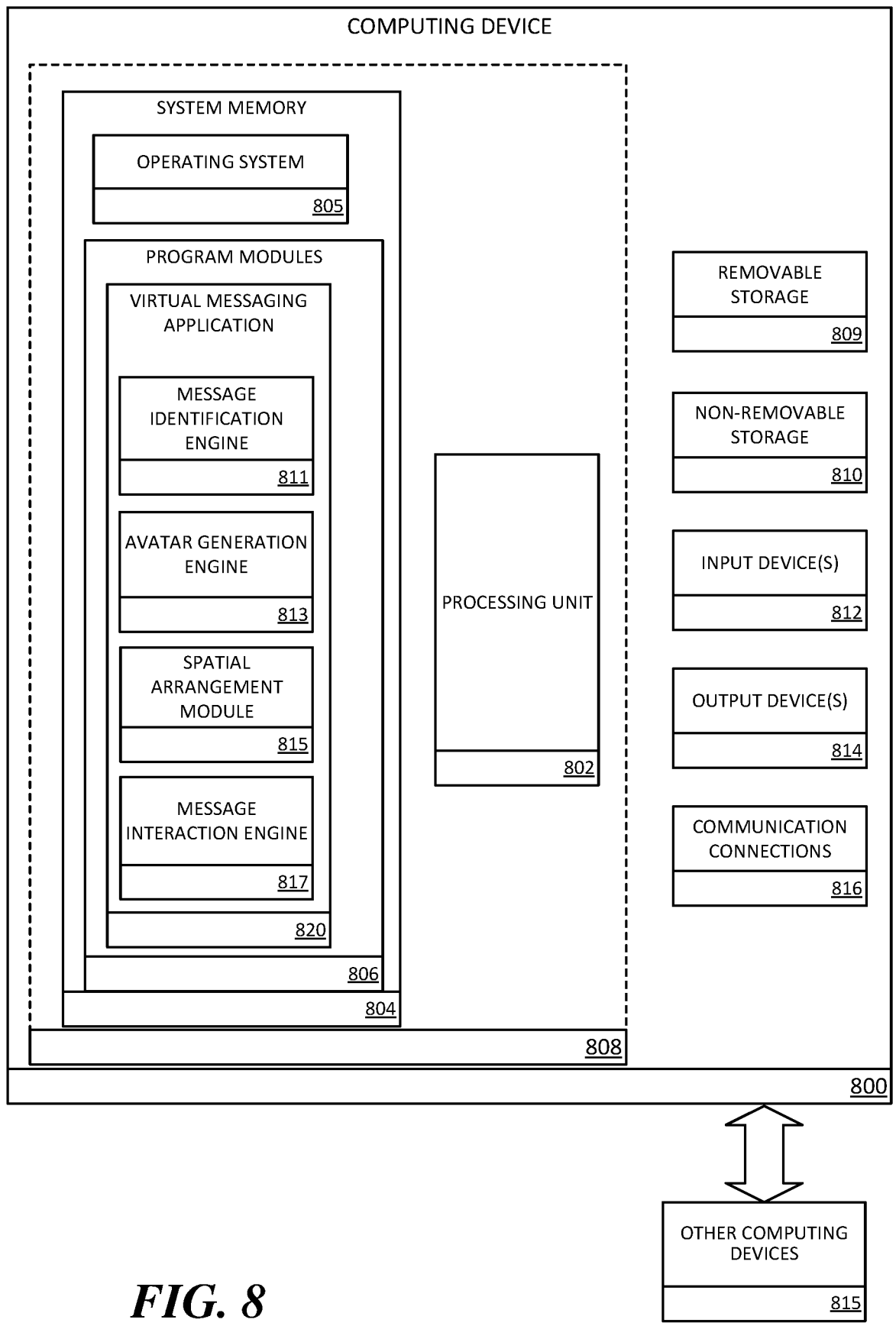
FIG. 8 is a block diagram illustrating example physical components of a computing device with which aspects of the disclosure may be practiced.

FIG. 8 is a block diagram illustrating physical components (e.g., hardware) of a computing device 800 with which aspects of the disclosure may be practiced. The computing device components described below may have computer executable instructions for performing one or more operations associated with presenting and interacting with electronic messages in a virtual space. In a basic configuration, the computing device 800 may include at least one processing unit 802 and a system memory 804. Depending on the configuration and type of computing device, the system memory 804 may comprise, but is not limited to, volatile storage (e.g., random access memory), non-volatile storage (e.g., read-only memory), flash memory, or any combination of such memories. The system memory 804 may include an operating system 805 suitable for running one or more virtual messaging programs. The operating system 805, for example, may be suitable for controlling the operation of the computing device 800. Furthermore, embodiments of the disclosure may be practiced in conjunction with a graphics library, other operating systems, or any other application program and is not limited to any particular application or system. This basic configuration is illustrated in FIG. 8 by those components within a dashed line 808. The computing device 800 may have additional features or functionality. For example, the computing device 800 may also include additional data storage devices (removable and/or non-removable) such as, for example, magnetic disks, optical disks, or tape. Such additional storage is illustrated in FIG. 8 by a removable storage device 809 and a non-removable storage device 810.

As stated above, a number of program modules and data files may be stored in the system memory 804. While executing on the processing unit 802, the program modules 806 (e.g., virtual messaging application 820) may perform processes including, but not limited to, the aspects, as described herein. According to examples, the message identification engine 811 may perform one or more operations associated with receiving account credentials associated with one or more electronic messaging services and retrieving one or more electronic messages from messaging services for which the account credentials provide access. The avatar generation engine 813 may perform one or more operation associated with causing a sender avatar associated with an electronic message to be displayed in a virtual space provided via a virtual messaging application executed on a client computing device, retrieving one or more pieces of information associated with a sending user corresponding to a sender avatar (retrieving information from one or more social network applications, retrieving presence information associated with a sending user's client computing device), and causing those one or more pieces of information associated with a sending user to be displayed in association with a corresponding sender avatar in a virtual space. Spatial arrangement module 815 may perform one or more operations related to spatially arranging one or more sender avatars based on a time that each electronic message corresponding to each of the one or more sender avatars was sent. The message interaction engine 817 may perform one or more operations related to causing selectable actions, which may be performed in association with one or more identified electronic messages, one or more sending users, and/or one or more sender avatars, to be displayed in a virtual space and/or executed upon receiving an indication from an accessing user's client computing device and a corresponding virtual messaging application to execute one or more of those actions.

Furthermore, embodiments of the disclosure may be practiced in an electrical circuit comprising discrete electronic elements, packaged or integrated electronic chips containing logic gates, a circuit utilizing a microprocessor, or on a single chip containing electronic elements or microprocessors. For example, embodiments of the disclosure may be practiced via a system-on-a-chip (SOC) where each or many of the components illustrated in FIG. 5 may be integrated onto a single integrated circuit. Such an SOC device may include one or more processing units, graphics units, communications units, system virtualization units and various application functionality all of which are integrated (or "burned") onto the chip substrate as a single integrated circuit. When operating via an SOC, the functionality, described herein, with respect to the capability of client to switch protocols may be operated via application-specific logic integrated with other components of the computing device 800 on the single integrated circuit (chip). Embodiments of the disclosure may also be practiced using other technologies capable of performing logical operations such as, for example, AND, OR, and NOT, including but not limited to mechanical, optical, fluidic, and quantum technologies. In addition, embodiments of the disclosure may be practiced within a general purpose computer or in any other circuits or systems.

The computing device 800 may also have one or more input device(s) 812 such as a keyboard, a mouse, a pen, a sound or voice input device, a touch or swipe input device, etc. The output device(s) 814 such as a display, speakers, a printer, etc. may also be included. The aforementioned devices are examples and others may be used. The computing device 800 may include one or more communication connections 816 allowing communications with other computing devices 850. Examples of suitable communication connections 816 include, but are not limited to, radio frequency (RF) transmitter, receiver, and/or transceiver circuitry; universal serial bus (USB), parallel, and/or serial ports.

The term computer readable media as used herein may include computer storage media. Computer storage media may include volatile and nonvolatile, removable and non-removable media implemented in any method or technology for storage of information, such as computer readable instructions, data structures, or program modules. The system memory 804, the removable storage device 809, and the non-removable storage device 810 are all computer storage media examples (e.g., memory storage). Computer storage media may include RAM, ROM, electrically erasable read-only memory (EEPROM), flash memory or other memory technology, CD-ROM, digital versatile disks (DVD) or other optical storage, magnetic cassettes, magnetic tape, magnetic disk storage or other magnetic storage devices, or any other article of manufacture which can be used to store information and which can be accessed by the computing device 800. Any such computer storage media may be part of the computing device 800. Computer storage media does not include a carrier wave or other propagated or modulated data signal.

Communication media may be embodied by computer readable instructions, data structures, program modules, or other data in a modulated data signal, such as a carrier wave or other transport mechanism, and includes any information delivery media. The term "modulated data signal" may describe a signal that has one or more characteristics set or changed in such a manner as to encode information in the signal. By way of example, and not limitation, communication media may include wired media such as a wired network or direct-wired connection, and wireless media such as acoustic, radio frequency (RF), infrared, and other wireless media.

Figure 9:
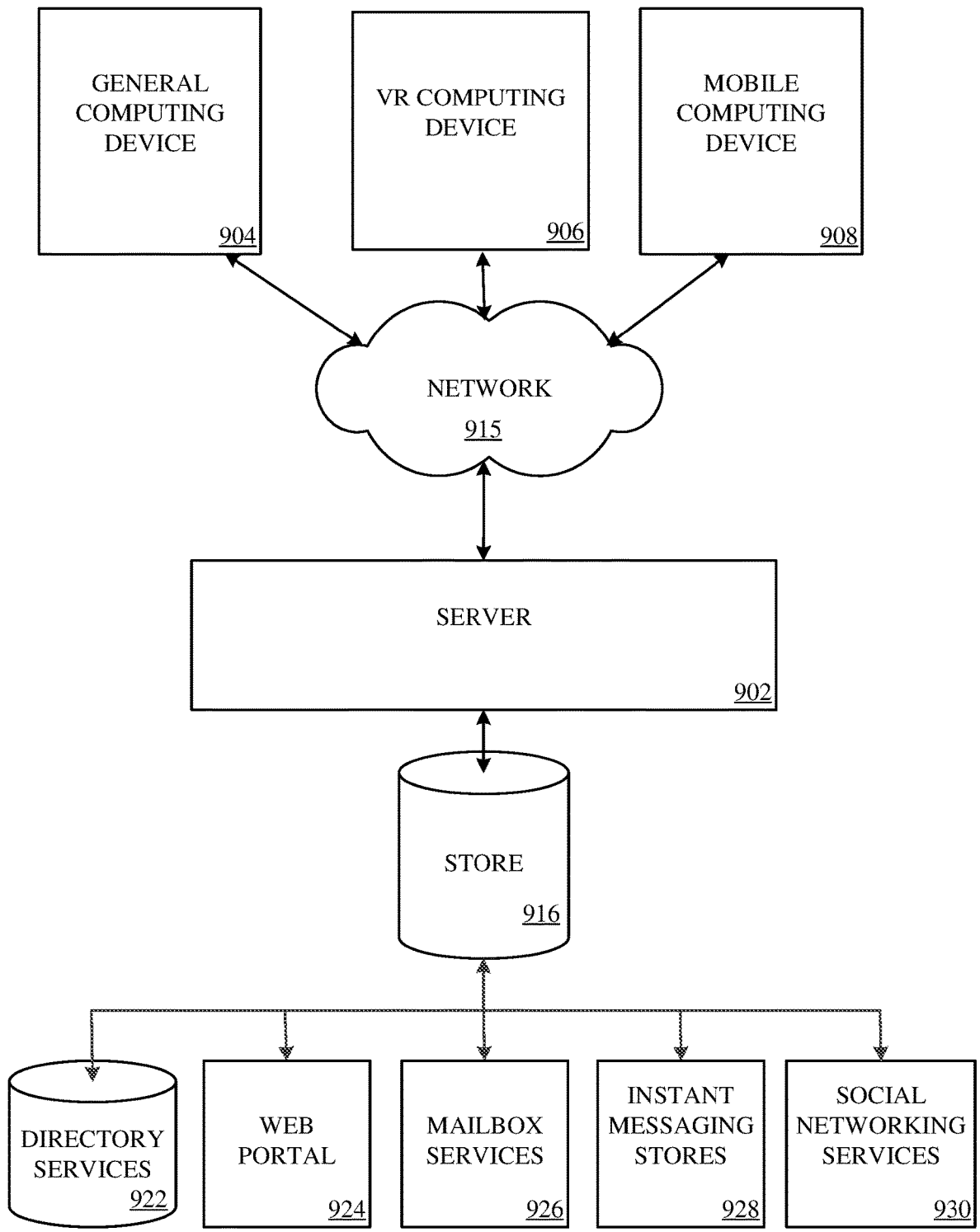
FIG. 9 is a simplified block diagram of a distributed computing system in which aspects of the present disclosure may be practiced.

FIG. 9 illustrates one aspect of the architecture of a system for processing data received at a computing system from a remote source, such as a personal/general computer 904, virtual reality computing device 906, or mobile computing device 908, as described above. Content displayed at server device 902 may be stored in different communication channels or other storage types. For example, various documents may be stored using a directory service 922, a web portal 924, a mailbox service 926, an instant messaging store 928, or a social networking site 930. The program modules 806 may be employed by a client that communicates with server device 902, and/or the program modules 806 may be employed by server device 902. The server device 902 may provide data to and from a client computing device such as a personal/general computer 904, a virtual reality computing device 906 and/or a mobile computing device 908 (e.g., a smart phone) through a network 915. By way of example, the computer system described above with respect to FIGS. 6-8 may be embodied in a personal/general computer 904, a virtual reality computing device 906 and/or a mobile computing device 908 (e.g., a smart phone). Any of these embodiments of the computing devices may obtain content from the store 916, in addition to receiving graphical data useable to be either pre-processed at a graphic-originating system, or post-processed at a receiving computing system.

Aspects of the present disclosure, for example, are described above with reference to block diagrams and/or operational illustrations of methods, systems, and computer program products according to aspects of the disclosure. The functions/acts noted in the blocks may occur out of the order as shown in any flowchart. For example, two blocks shown in succession may in fact be executed substantially concurrently or the blocks may sometimes be executed in the reverse order, depending upon the functionality/acts involved.

The description and illustration of one or more aspects provided in this application are not intended to limit or restrict the scope of the disclosure as claimed in any way. The aspects, examples, and details provided in this application are considered sufficient to convey possession and enable others to make and use the best mode of claimed disclosure. The claimed disclosure should not be construed as being limited to any aspect, example, or detail provided in this application. Regardless of whether shown and described in combination or separately, the various features (both structural and methodological) are intended to be selectively included or omitted to produce an embodiment with a particular set of features. Having been provided with the description and illustration of the present disclosure, one skilled in the art may envision variations, modifications, and alternate aspects falling within the spirit of the broader aspects of the general inventive concept embodied in this application that do not depart from the broader scope of the claimed disclosure.

The various embodiments described above are provided by way of illustration only and should not be construed to limit the claims attached hereto. Those skilled in the art will readily recognize various modifications and changes that may be made without following the example embodiments and applications illustrated and described herein, and without departing from the true spirit and scope of the following claims.

What is claimed is:

1. A method for interacting with one or more electronic messages, the method comprising:
   receiving a message query comprising one or more search terms;

determining that a first electronic message thread is more relevant to the message query than a second electronic message thread;

causing the first electronic message thread to be displayed on a display of a computing device, the first electronic message thread comprising a first plurality of electronic messages displayed in association with a first plurality of avatars, wherein each of the first plurality of avatars represents a sender of one of the first plurality of electronic messages;

causing the second electronic message thread to be displayed on the display of the computing device, the second electronic message thread comprising a second plurality of electronic messages displayed in association with a second plurality of avatars, wherein each of the second plurality of avatars represents a sender of one of the second plurality of electronic messages, and wherein the avatars corresponding to the second electronic message thread are displayed further away from a virtual instance of a user of the computing device than the avatars corresponding to the first electronic message thread based on their relative relevance to the message query;

receiving a first indication that the virtual instance of the user of the computing device has crossed a first virtual threshold distance to one of the avatars;

causing, based on the received first indication, a first set of information associated with the one of the avatars to be displayed on the display of the computing device;

receiving a second indication that the virtual instance of the user of the computing device has crossed a second virtual threshold distance to the one of the avatars;

causing, based on the received second indication, a second set of information associated with the one of the avatars to be displayed on the display of the computing device;

causing, in association with the one of the avatars, a selectable option to have a corresponding one of the first plurality of electronic messages presented in a virtual space by the computing device to be displayed on the display of the computing device;

receiving an indication to present the corresponding electronic message in the virtual space; and causing the corresponding electronic message to be presented by the computing device in the virtual space.

2. The method of claim 1, wherein the first plurality of avatars are spatially arranged in the virtual space relative to one another based on a time that each of the first plurality of electronic messages was sent.

3. The method of claim 1, wherein the selectable option comprises a prompt to have the corresponding one of the first plurality of electronic messages audibly communicated by a corresponding avatar in the virtual space.

4. The method of claim 1, wherein the selectable option comprises a prompt to visually display at least a portion of the corresponding one of the first plurality of electronic messages in the virtual space.

5. The method of claim 1, wherein the selectable option is displayed upon the virtual instance of a user of the computing device coming within the second virtual threshold distance of the one of the avatars in the virtual space.

6. The method of claim 1, wherein the computing device is one of: a virtual reality computing device, and an augmented reality computing device.

7. The method of claim 1, further comprising: causing an attachment to a corresponding one of the first plurality of electronic messages to be displayed in association with one of the first plurality of avatars in the virtual space.

8. A system for interacting with one or more electronic messages, comprising:

a memory for storing executable program code; and one or more processors, functionally coupled to the memory, the one or more processors being responsive to computer-executable instructions contained in the program code and operative to:

receive a message query comprising one or more search terms;

determine that a first electronic message thread is more relevant to the message query than a second electronic message thread;

cause the first electronic message thread to be displayed by a virtual reality computing device, the first electronic message thread comprising a first plurality of electronic messages displayed in association with a first plurality of avatars, wherein each of the first plurality of avatars represents a sender of one of the first plurality of electronic messages;

cause the second electronic message thread to be displayed by the virtual reality computing device, the second electronic message thread comprising a second plurality of electronic messages displayed in association with a second plurality of avatars, wherein each of the second plurality of avatars represents a sender of one of the second plurality of electronic messages, and wherein the avatars corresponding to the second electronic message thread are displayed further away from a virtual instance of a user of the virtual reality computing device than the avatars corresponding to the first electronic message thread based on their relative relevance to the message query;

receive a first indication that the virtual instance of the user of the computing device has crossed a first virtual threshold distance to one of the avatars;

cause, based on the received first indication, a first set of information associated with the one of the avatars to be displayed by the virtual reality computing device;

receive a second indication that the virtual instance of the user of the virtual reality computing device has crossed a second virtual threshold distance to the one of the avatars;

cause, based on the received second indication, a second set of information associated with the one of the avatars to be displayed by the virtual reality computing device;

cause, in association with the one of the first plurality of avatars, a selectable option to have a corresponding one of the first plurality of electronic messages presented in a virtual space to be displayed by the virtual reality computing device;

receive, by the virtual reality computing device, an indication to present the corresponding electronic message in the virtual space; and cause the corresponding electronic message to be presented in the virtual space by the virtual reality computing device.

9. The system of claim 8, wherein the first plurality of avatars are spatially arranged in the virtual space relative to one another based on a time that each of the first plurality of electronic messages was sent.

10. The system of claim 8, wherein the selectable option comprises a prompt to have a corresponding one of the first plurality of electronic messages audibly communicated by a corresponding avatar.

11. The system of claim 8, wherein the selectable option comprises a prompt to visually display at least a portion of the corresponding one of the first plurality of messages in the virtual space.

12. The system of claim 8, wherein the selectable option is displayed upon the virtual instance of the user in the virtual space coming within the second virtual threshold distance of the one of the avatars in the virtual space.

13. The system of claim 8, wherein the selectable option is displayed upon receiving, by the virtual reality computing device, one of: a verbal command to view the selectable option within the virtual space, a gesture command to view the selectable option within the virtual space.

14. The system of claim 8, wherein the one or more processors are further responsive to the computer-executable instructions contained in the program code and operative to:
cause the corresponding electronic message to be presented in the virtual space in response to receiving, by the virtual reality computing device, a gesture input to view at least a portion of the corresponding one of the plurality of messages.

15. A computer-readable hardware storage device comprising executable instructions that, when executed by one or more processors, assist with interacting with one or more electronic messages in a virtual space of a client computing device, the computer-readable storage device including instructions executable by the one or more processors for:
receiving credentials associated with an electronic messaging account;
receiving a message query comprising one or more search terms;
identifying a first plurality of electronic messages of a first message thread sent to a user associated with the electronic messaging account;
identifying a second plurality of electronic messages of a second message thread sent to a user associated with the electronic messaging account;
determining that the first electronic message thread is more relevant to the message query than the second electronic message thread;
causing, in the virtual space, a first plurality of avatars to be displayed, wherein each of the first plurality of avatars represents a sender of at least one of the first plurality of electronic messages;
causing, in the virtual space, a second plurality of avatars to be displayed, wherein each of the second plurality of avatars represents a sender of at least one of the second plurality of electronic messages, and wherein the avatars corresponding to the second electronic message thread are displayed further away from a virtual instance of a user of the client computing device than the avatars corresponding to the first electronic message thread based on their relevance to the message query;
receiving a first indication that the virtual instance of the user of the client computing device has crossed a first virtual threshold distance to one of the avatars;
causing, in the virtual space, based on the received first indication, a first set of information associated with the one of the avatars to be displayed;
receiving a second indication that the virtual instance of the user of the client computing device has crossed a second virtual threshold distance to the one of the avatars;
causing, in the virtual space, based on the received second indication, a second set of information associated with the one of the avatars to be displayed;
receiving, from the client computing device, an indication to have one of the first plurality of electronic messages presented in association with a corresponding one of the first plurality of avatars; and
causing the indicated electronic message to be presented, by the client computing device, in association with the corresponding avatar.

16. The computer-readable hardware storage device of claim 15, wherein the instructions are further executable by the one or more processors for:
spatially arranging, in the virtual space, the first plurality of avatars corresponding to the first plurality of electronic messages, relative to one another, based on a time that each of the electronic messages of the first plurality of electronic messages were sent; and
spatially arranging, in the virtual space, the second plurality of avatars corresponding to the second plurality of electronic messages, relative to one another, based on a time that each of the electronic messages of the second plurality of electronic messages were sent.

17. The computer-readable hardware storage device of claim 15, wherein the instructions are further executable by the one or more processors for causing, in the virtual space, a menu to be displayed in association with one of the first plurality of avatars, wherein the menu comprises a plurality of selectable options, each of the selectable options being executable, by the computer-readable storage device, for implementing at least one action associated with a corresponding one of the first plurality of electronic messages.

18. The computer-readable hardware storage device of claim 17, wherein the plurality of selectable options comprise at least one of: an option to audibly read the corresponding one of the plurality of electronic messages by a sending avatar of the corresponding one of the plurality of electronic messages; an option to display, in the virtual space, at least a portion of the corresponding one of the plurality of electronic messages; an option to open, in the virtual space, a text messaging dialog between the user associated with the electronic messaging account and a sender of the corresponding one of the plurality of electronic messages; an option to open, in the virtual space, a video dialog between the user associated with the electronic messaging account and a sender of the corresponding one of the plurality of electronic messages; an option to open, in association with the virtual space, an audio dialog between the user associated with the electronic messaging account and a sender of the corresponding one of the plurality of electronic messages; and an option to view, in the virtual space, an attachment to the corresponding one of the plurality of electronic messages.

* * * * *